US011883416B2

(12) United States Patent
Casal Álvarez et al.

(10) Patent No.: US 11,883,416 B2
(45) Date of Patent: Jan. 30, 2024

(54) METHODS AND COMPOSITIONS FOR THE TREATMENT OF IL13RA2—OVEREXPRESSING CANCER

(71) Applicant: CONSEJO SUPERIOR DE INVESTIGACIONES CIENTÍFICAS (CSIC), Madrid (ES)

(72) Inventors: José Ignacio Casal Álvarez, Madrid (ES); Rubén Álvaro Bartolomé Conde, Madrid (ES)

(73) Assignee: CONSEJO SUPERIOR DE INVESTIGACIONES CIENTÍFICAS (CSIC), Madrid (ES)

( * ) Notice: Subject to any disclaimer, the term of this patent is extended or adjusted under 35 U.S.C. 154(b) by 111 days.

(21) Appl. No.: 17/541,924

(22) Filed: Dec. 3, 2021

(65) Prior Publication Data
US 2022/0233552 A1 Jul. 28, 2022

Related U.S. Application Data

(60) Provisional application No. 63/121,790, filed on Dec. 4, 2020.

(51) Int. Cl.
A61P 35/00 (2006.01)
A61K 31/575 (2006.01)

(52) U.S. Cl.
CPC ............ A61K 31/575 (2013.01); A61P 35/00 (2018.01)

(58) Field of Classification Search
CPC .............................. A61P 35/00; A61K 31/575
See application file for complete search history.

(56) References Cited

PUBLICATIONS

Debinski, Waldemar, et al., "Molecular Expression Analysis of Restrictive Receptor for Interleukin 13, a Brain Tumor-associated Cancer/Testis Antigen," Molecular Medicine 6(5): Jan. 25, 2000, pp. 440-449.
Debinski, Waldemar, et al., "Receptor for Interleukin 13 is a Marker and Therapeutic Target for Human High-Grade Gliomas,"Clinical Cancer Research, vol. 5, May 1999, pp. 985-990.
Fujisawa, Toshio, et al., "A Novel Role of Interleukin-13 Receptor α2 in Pancreatic Cancer Invasion and Metastasis," Experimental Therapeutics, Molecular Targets, and Chemical Biology, Cancer Res 2009; 69: (22), Nov. 15, 2009, pp. 8678-8685.
Bernard, Jérôme, et al., "Expression of Interleukin 13 Receptor in Glioma and Renal Cell Carcinoma: IL13Rα2 as a Decoy Receptor for IL13," Laboratory Investigation, vol. 81, No. 9, Sep. 2001, 9 pages.
Beard, Rachel E., "Gene Expression Profiling using Nanostring Digital RNA Counting to Identify Potential Target Antigens for Melanoma Immunotherapy," Clin Cancer Res; 19(18), Sep. 16, 2013, pp. 4941-4950.

Takenouchi, Makoto, et al., "Epigenetic Modulation Enhances the Therapeutic Effect of Anti-IL-13Rα2 Antibody in Human Mesothelioma Xenografts," Clin Cancer Res; 17(9), Feb. 28, 2011, pp. 2819-2829.
Kawakami, Mariko, et al., "Interleukin-13 Receptor α2 Chain in Human Head and Neck Cancer Serves as a Unique Diagnostic Marker," Clinical Cancer Research, vol. 9, Dec. 15, 2003, pp. 6381-6388.
Kioi, Mitomu, et al., "Interleukin-13 Receptor α2 Chain, A Potential Biomarker and Molecular Target for Ovarian Cancer Therapy," American Cancer Society, vol. 107, No. 6, Sep. 15, 2006, pp. 1407-1418.
Hallett, Miranda A., et al., "Cytokine Stimulation of Epithelial Cancer Cells: The Similar and Divergent Functions of IL-4 and IL-13," Cancer Res; 72(24), Dec. 15, 2012, pp. 6338-6343.
Barderas, Rodrigo, et al., "High Expression of IL-13 Receptor α2 in Colorectal Cancer is Associated with Invasion, Liver Metastasis, and Poor Prognosis, " Cancer Res; 72(11), Jun. 1, 2012, pp. 2780-2789.
Fujisawa, Toshio, et al., "IL-13 regulates cancer invasion and metastasis through IL-13Rα2 via ERK-AP-1 pathway in mouse model of human ovarian cancer," Int. J. Cancer: 131, 2012, pp. 344-356.
Lal, Anita, et al., "Mutant Epidermal Growth Factor Receptor Up-Regulates Molecular Effectors of Tumor Invasion," Cancer Research 62, Jun. 15, 2002, pp. 3335-3339.
Brown, Christine E., "Glioma IL13Rα2 is Associated with Mesenchymal Signature Gene Expression and Poor Patient Prognosis," PLOS One, Oct. 2013, vol. 8, Issue 10, 14 pages.
Kawakami, Mariko, et al., "Analysis of Interleukin-13 Receptor α2 Expression in Human Pediatric Brain Tumors," American Cancer Society, vol. 101, No. 5, Sep. 1, 2004, pp. 1036-1042.
Jarboe, John S., et al., "Expression of Interleukin-13 Receptor α2 in Glioblastoma Multiforme: Implications for Targeted Therapies, " Cancer Res 2007; 67 (17), Sep. 1, 2007, pp. 7983-7986.
Stupp, MD, Roger, et al., "Effect of Tumor-Treating Fields Plus Maintenance Temozolomide vs Maintenance Temozolomide Alone on Survival in Patients With Glioblastoma, A Randomized Clinical Trial," JAMA, vol. 318, No. 23, Dec. 19, 2017, pp. 2306-2316.
Thaci, Bart, et al., "Significance of interleukin-13 receptor alpha 2—targeted glioblastoma therapy," Neuro-Oncology 16(10), Feb. 24, 2014, pp. 1304-1312.
Fichtner-Feigl, Stefan, et al., "IL-13 signaling through the IL-13α$_2$ receptor is involved in induction of TGF-β$_1$ production and fibrosis," Nature Medicine, vol. 12, No. 1, Jan. 2006, pp. 99-106.
Bhardwaj, Rukmini, et al., "Identification of a novel role of IL-13Ra2 in human Glioblastoma multiforme: interleukin-13 mediates signal transduction through AP-1 pathway," Journal of Translational Medicine, (2018) 16:369, 13 pages.

(Continued)

Primary Examiner — Bruck Kifle
(74) Attorney, Agent, or Firm — WOMBLE BOND DICKINSON (US) LLP

(57) ABSTRACT

The invention relates to methods and compositions for treatment of IL13Rα2-overexpressing cancer, wherein the treatment comprises administering a protein tyrosine phosphatase-1B (PTP1B) inhibitor.

2 Claims, 22 Drawing Sheets
Specification includes a Sequence Listing.

(56) References Cited

PUBLICATIONS

Bartolomé, Rubén A., et al., "IL13 Receptor α2 Signaling Requires a Scaffold Protein, FAM120A to Activate the FAK and PI3K Pathways in Colon Cancer Metastasis," Cancer Res; 75(12), Jun. 15, 2015, pp. 2434-2444.

Bartolomé, Rubén A., et al., "An IL13Ra2 peptide exhibits therapeutic activity against metastatic colorectal cancer," British Journal of Cancer, Oct. 15, 2018, pp. 940-949.

Lessard, Laurent, et al., "The two faces of PTP1B in cancer," Biochimica et Biophysica Acta 1804, (2010), pp. 613-619.

Chen, Queting, et al., "Overexpression of PTP1B in human colorectal cancer and its association with tumor progression and prognosis," J. Mol. Hist. (2014), 45, pp. 153-159.

Lessard, Laurent, et al., "PTP1B is an Androgen Receptor-Regulated Phosphatase That Promotes the Progression of Prostate Cancer," Cancer Res; 72(6), Mar. 15, 2012, pp. 1529-1537.

Wiener, Jon R., "Overexpression of the tyrosine phosphatase PTP1B is associated with human ovarian carcinomas," Am. J. Obstet. Gynecol., vol. 107, No. 4, Apr. 1994, pp. 1177-1183.

Wang, Jinguo, et al., "PTP1B expression contributes to gastric cancer progression," Med. Oncol. (2012) 29, pp. 948-956.

Wang, Na, et al., "Frequent amplification of *PTP1B* is associated with poor survival of gastric cancer patients," Cell Cycle 14:5, Mar. 1, 2015, pp. 732-743.

Bjorge, Jeffrey D., et al., "Selected glimpses into the activation and function of Src kinase," Oncogene (2000) 19, pp. 5620-5635.

Garaud, Mathieu, et al., "Substrate Profiling of Protein Tyrosine Phosphatase PTP1B by Screening a combinatorial Peptide Library," J. Am. Chem. Soc., 2007, 129, pp. 5366-5367.

Qin, Zhaohong, et al., "Functional properties of Claramine: A novel PTP1B inhibitor and insulin-mimetic compound," Biochemical and Biophysical Research Communications 458, (2015), pp. 21-27.

Lantz, Kristen A., et al., "Inhibition of PTP1B by Trodusquemine (MSI-1436) Causes Fat-specific Weight Loss in Diet-induced Obese Mice," Integrative Physiology, vol. 18, No. 8, Aug. 2010, pp. 1516-1523.

Yamada, Marina, et al., "Implanted cannula-mediated repetitive administration of AB25-35 into the mouse cerebral ventricle effectively impairs spatial working memory," Behavioural Brain Research 164 (2005), pp. 139-146.

Hoekstra, Elmer, et al., "Increased PTP1B expression and phosphatase activity in colorectal cancer results in a more invasive phenotype and worse patient outcome," Oncotarget, vol. 7, No. 16, Mar. 1, 2016, pp. 21922-21938.

Wiener, Jon R., "Overexpression of the Protein Tyrosine Phsphatase PTP1B in Human Breast Cancer: Association With p185$^{c-erbB-2}$ Protein Expression," Journal of the National Cancer Institute, vol. 86, No. 5, Mar. 2, 1994, pp. 372-378.

Balyasnikova, Irina V., et al., "Characterization and Immunotherapeutic Implications for a Novel Antibody Targeting Interleukin (IL)-13 Receptor α2," The Journal of Biological Chemistry, vol. 287, No. 36, Aug. 31, 2012, pp. 30215-30227.

Newman, Jennifer P., et al., "Interleukin-13 receptor alpha 2 cooperates with EGFRvIII signaling to promote glioblastoma multiforme," Nature Communications | 8:1913, 2017, 17 pages.

SEQUENCE LISTING

<160> NUMBER OF SEQ ID NOS: 4

<210> SEQ ID NO 1
<211> LENGTH: 39
<212> TYPE: DNA
<213> ORGANISM: Artificial Sequence
<220> FEATURE:
<223> OTHER INFORMATION: Oligonucleotide used for mutagenesis

<400> SEQUENCE: 1
cttttgcgta agccaaagag gttcccaaaa atgattcca                      39

<210> SEQ ID NO 2
<211> LENGTH: 41
<212> TYPE: DNA
<213> ORGANISM: Artificial Sequence
<220> FEATURE:
<223> OTHER INFORMATION: Oligonucleotide used for mutagenesis

<400> SEQUENCE: 2
aaaattctgg aatcattttt gggaaggtgt ttggcttacg c                   41

<210> SEQ ID NO 3
<211> LENGTH: 23
<212> TYPE: DNA
<213> ORGANISM: Artificial Sequence
<220> FEATURE:
<223> OTHER INFORMATION: EGFR siRNA

<400> SEQUENCE: 3
ugugccaccu gugccauccd tdt                                       23

<210> SEQ ID NO 4
<211> LENGTH: 17
<212> TYPE: PRT
<213> ORGANISM: Homo sapiens

<400> SEQUENCE: 4

Arg Lys Pro Asn Thr Tyr Pro Lys Met Ile Pro Glu Phe Phe Cys Asp
1               5                   10                  15

Thr

METHODS AND COMPOSITIONS FOR THE TREATMENT OF IL13RA2—OVEREXPRESSING CANCER

CROSS-REFERENCE TO RELATED APPLICATIONS

The present patent application claims priority to U.S. Provisional Application No. 63/121,790 filed Dec. 4, 2020, the disclosure of which are incorporated herein by reference.

INCORPORATION BY REFERENCE

The content of the ASCII text file of the sequence listing named "Sequence_Listing", which is 2 kb in size, was created on and electronically submitted via EFS-Web Dec. 3 2021, is incorporated herein by reference in its entirety.

FIELD

The invention relates to methods and compositions for treatment of IL13Rα2-overexpressing cancer, wherein the treatment comprises administering a protein tyrosine phosphatase-1B (PTP1B) inhibitor.

BACKGROUND ART

IL13Rα2 (UniProtKB ID Q14627; version 192) has been classified as a cancer/testis-like tumor antigen encoded in chromosome X[1]. In normal tissues, IL13Rα2 is mainly expressed in the testis. However, IL13Rα2 is overexpressed in a variety of tumor types such as colorectal cancer (CRC), renal cell carcinoma, pancreatic, melanoma, head and neck, mesothelioma, ovarian cancer (OC) and glioblastoma (GBM), among others [2-9]. In CRC, a statistically-significant association was observed between IL13Rα2 expression and tumor progression (T stage), with higher expression in T3 or T4 tumors as compared with T1 or T2 [10]. In ovarian cancer (OC), IL-13 was described to regulate cancer invasion and metastasis through IL13Rα2 [11]. In GBM, IL13Rα2 is upregulated following the expression of mutant EGFRvIII [12], being overexpressed in 58% of adult and 83% of pediatric brain tumors [13, 14]. Furthermore, IL13Rα2 expression in GBM has been associated with an increased malignancy grade, an aggressive mesenchymal gene expression signature, and a poorer patient prognosis [15]. Despite advances in neurosurgery and adjuvant treatment, the median survival of patients with GBM is only about 21 months and no improvements in overall patient survival have been obtained in the last 50 years [16].

Due to the specific expression in cancer cells, IL13Rα2 has been validated as target for cancer therapy in multiple studies and trough different approaches [17]. Initially, the IL-13/IL-13Rα2 axis was demonstrated to mediate signaling through AP-1 transcriptional pathway in a number of human cancers [3, 11, 18, 19]. The AP-1 pathway lies at the bottom of the Ras→Raf→MAPK cascade. In CRC cells, the binding of IL-13 to IL13Rα2 triggers STATE-independent cellular pathways, promoting migration, invasion and survival of cancer cells through the scaffold protein FAM120A, which participates in the activation of FAK and the PI3K pathway [10, 20]. Therefore, IL-13/IL-13Rα2 use the PI3K/AKT/mTOR and MAP kinases signaling that, in turn, induces the activation of the AP-1 complex to promote human cancer metastasis. However, the connection between IL13Rα2 and Src was unclear, as the IL13Rα2 cytoplasmic domain is relatively short for stable protein-protein interactions. The inventors of the present application have recently reported that FAM120A may act as a bridge between IL13Rα2 and Src [20]. Furthermore, a candidate IL13 Ra2 therapeutic peptide was able to inhibit IL-13 signaling capacity in both tumors, CRC and glioblastoma, by inhibiting the Src pathway [21].

Protein-tyrosine phosphatases (PTPs) work in a coordinated way to regulate tyrosine kinases phosphorylation and, consequently, several fundamental physiological processes. Among them, PTP1B (UniProtKB ID P18031; version 243) is a multifunctional protein associated to the glucose metabolism that plays a key role in multiple diseases like obesity, diabetes or cancer [22]. Increased PTP1B expression has been reported in colorectal [23, 24], prostate [25], breast [26], ovarian [27] and gastric [28] cancers. In colorectal and gastric cancer, increased expression of PTP1B was associated to tumor progression and poor patient outcome [29, 30]. PTP1B promotes proliferation and metastasis through the activation of Src/Ras/ERK and PI3K/AKT signalling pathways [31], in a similar way to IL-13.

Despite the extensive research efforts in the field, the specific role of PTP1B in ca ncer and the mechanism by which it exerts its biological effect is still unknown. A better understanding of the IL13Rα2 signalling pathway and the role of PTP1B in it would thus prove incredibly helpful in facilitating the discovery of novel therapeutic candidates in those cancers presenting overexpression of IL13Rα2.

SUMMARY OF THE INVENTION

The inventors of the present application have discovered and characterized for the first time the interaction between PTP1B and IL3Rα2. This application provides evidence that PTP1B mediates IL13Rα2 pro-tumorigenic activities, proving its value as a novel therapeutic target to inhibit IL13Rα2 signalling.

Thus, the present invention relates to a method of treatment of IL13Rα2-overexpressing cancer in a subject, wherein the treatment comprises administering to said subject an effective amount of a protein tyrosine phosphatase-1 B (PTP1B) inhibitor.

The subject is preferably a mammal, and more preferably, a human being.

The term "effective amount" means the amount of PTP1B inhibitor that elicits the biological or medical response of a tissue, system, animal or human that is being sought by the researcher, veterinarian, medical doctor or other clinician. In the context of the present invention, the biological or medical response to elicit is the treatment and/or prevention of IL13Rα2-overexpressing cancer.

The PTP1B inhibitor may be any molecule capable of completely or partially inhibiting the biological activity of PTP1B by any mode of action, including but not limited to preventing the expression product of the PTP1B gene from being produced (interrupting the PTP1B transcription and/or blocking the translation of the mRNA coming from the PTP1B gene expression) and directly inhibiting the PTP1B biological activity, for example, and among others, by binding to PTP1B or its receptor.

By way of non-limiting examples, the PTP1B inhibitor may be a small molecule inhibitor or an antibody or fragment thereof.

Small molecule inhibitors for use in the method of the invention include, but are not limited to, Claramine (PubChem SID 434128162) [32] and Trodusquemine (PubChem CID 9917968) [33].

The term "overexpressing" refers to an increased expression level of the gene encoding IL13Rα2 with respect to a reference level in healthy individuals.

The inhibitor may be used in different types of cancer.

By way of non-limiting examples, the PTP1B inhibitor may be used in glioblastoma (GBM), metastatic colorectal cancer (CRC) and ovarian cancer (OC).

The PTP1B inhibitor may be administered by any standard routes of administration. By way of non-limiting examples, the PTP1B inhibitor may be administered intravenously.

The inhibitors for use in the present invention can be incorporated into pharmaceutical compositions for its administration to the subject.

Additionally, the efficacy of the inhibitor fora more efficient administration and cellular entry may be optimized in any way. For example, and without any limiting effect, the inhibitor may be administered as liposomes, nanoparticles or micropumps.

The specific dose level and frequency of dosage for any particular patient may be varied and will depend upon a variety of factors. An appropriate dosage level of the inhibitor of the invention will generally be about 0.01 to 50 mg per kg patient body weight per day which can be administered in single or multiple doses.

The inhibitor of the present invention may be used in combination with one or more other drugs.

Unless otherwise defined, all technical and scientificterms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and drawings are provided by way of illustration and are not intended to be limiting of the present invention.

BRIEF DESCRIPTION OF THE DRAWINGS

FIG. 2B shows colorectal cancer, FIG. 2C shows glioblastoma and FIG. 2D shows ovarian cancer patients, according to PTP1B mRNA expression. Significant associations of PTP1B expression with lower overall survival were found in the three types of cancer using the log-rank statistical method.

FIG. 4A shows anaylsis of Src and PTP1B association by immunoprecipitation and Western blot. FIG. 4B shows KM12SM, U87MG and A2780 cells were transfected with control or PTP1B-targeted siRNAs, exposed to IL-13, lysed and the extracts analyzed by Western blot to detect $pSrc\ Y_{530}$ and total Src. FIG. 4C shows KM12SM, SW620, U87MG and U118MG cells transfected with the same siRNAs were exposed to IL-13 for the indicated times and the cell extracts were analyzed for FAK, Src, AKT and ERK1/2 phosphorylation by Western blot. RhoGDI was used as loading control.

FIG. 7A shows RT-PCR assays of RNA isolated from livers to detect human GAPDH as a surrogate of liver colonization by KM12SM cells previously transfected with the indicated siRNAs. Murine β-actin amplification was used as a loading control. FIG. 7B shows Kaplan-Meier survival analysis for mice inoculated intrasplenically with metastatic KM12SM cells and treated with Claramine. Treatment significantly increased mice survival (***, $p<0.001$). FIG. 7C shows mice were subcutaneously inoculated with U251 cells and treated with PBS or Claramine after 15 days of implantation. Claramine significantly inhibited tumor growth (*, p<0.05; *, p<0.001). FIG. 7D shows mouseweight during the treatment with Claramine remained constant. FIG. 7E shows Kaplan-Meier survival analysis for mice inoculated intracranially with GBM12 PDX cells. Treatment with Claramine started 7 days after tumor implantation and significantly increased mice survival (*, p<0.001).

EXAMPLES

Material and Methods

Figure 1A:
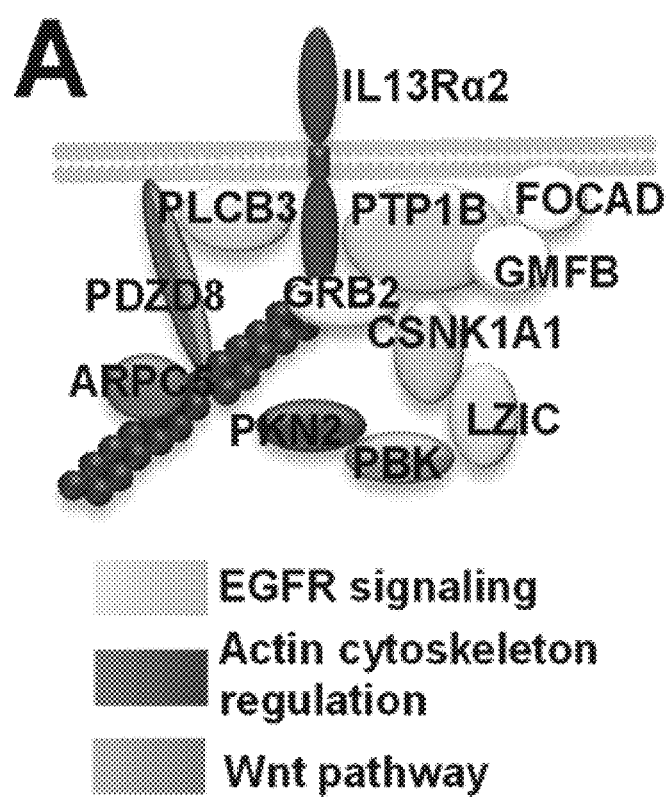
FIG. 1. A shows protein interaction network for IL13Rα2 in U251 cells was identified by mass spectrometry analysis. Protein position was tentatively assigned based on existing literature.
FIG. 1B shows Western blot analysis of the expression of PTP1B in human CRC, OC and GMB cell lines and PDXs (GBM43 and GBM6).
FIG. 1C shows Western blot analysis of IL13Rα2 (top) and PTP1B (bottom) co-immunoprecipitated proteins in the indicated cell lines.
FIG. 1D shows PEP-FOLD3 representation of IL13Rα2 cytoplasmic tail structure showing the $Tyr_{369}$ location (SEQ ID NO: 4). Colorectal RKO cancer cells transfected with empty vectors (mock) or vectors encoding for wild type IL13Rα2 or Y369F mutated form were lysed and subjected to Western blot analysis as shown in FIG. 1E to verify the expression of PTP1B and IL13Rα2 forms and IL13Rα2 immunoprecipitation for the detection of coimmunoprecipitated PTP1B as shown in FIG. 1F.
FIG. 1G shows same RKO transfectants were subjected to invasion through Matrigel. Whereas IL-13 promoted cell invasion of IL13Rα2 WT cells (***, $p<0.001$), the $Tyr_{369}$ mutant significantly inhibited the invasion (000, $p<0.001$).

Cell culture, PDXs, and reagents.

Highly metastatic KM12SM human colon cancer cells were obtained from Dr. I. Fidler (MD Anderson Cancer Center. Houston, TX, USA). U87MG and U118MG glioblastoma cell lines were provided by Dr. G. Velasco (UCM, Madrid, Spain). Ovarian cancer cells A2780 were provided by Dr. F. Diaz-Pereira (CIB) and SKOV3 by Dr. A. I. Torres (UCM). Human SW480, SW620 and RKO colon cancer, OVCAR3 ovarian and U251 MG GBM cell lines were purchased from the ATCC and passaged less than 6 months after purchase for all the experiments. All cell lines were cultured in DMEM (Invitrogen) containing 10% FCS (Invitrogen) and antibiotics at 37° C. in a 5% $CO_2$ humidified atmosphere. Tumor sample lysates from GBM6, GBM43 and GBM12 PDX glioblastoma lines were kindly provided by Dr. C. D. James (Northwestern University, Chicago, USA).

Human and murine IL-13 were used at 10 ng/ml and EGF at 50 ng/ml. These proteins were purchased from PeproTech. Claramine ((3β, 6β)-6-[[3-[[4-[(3-Aminopropyl) amino] butyl]amino]propyl]amino]-cholestan-3-ol trifluoroacetate salt; Sigma-Aldrich, SML1545) was used at 2 μM for in vitro assays and 25-49 μg/mice for in vivo assays.

Mutagenesis of IL13Rα2 and siRNA transfections.

For IL13Rα2 $Tyr_{369}$(TAC)-Phe(TTC) mutagenesis, vectors encoding for full-length IL13Rα2 (IMAGE collection) were subjected to mutagenesis using QuickChange Lightning Site-Directed Mutagenesis Kit (Agilent Technologies) using oligonucleotides: 5'-CTTTTGCGTAAGCCAAAGA-GGTTCCCAAAAATGATTCCA-3' (SEQ ID NO: 1) and 5'-AAAATTCTGGAATCATTTTT-GG-GAAGGTGTTTGGCTTACGC-3' (SEQ ID NO: 2) according to manufacturers instructions. Mutation was confirmed by in-house sequencing. Different siRNAs targeting PTP1B (#1 SASI-Hs01-00230698 and #2 SASI-Hs02-00334527), EGFR (5'-UGUGCCACCUGUGCCAUCCdTdT-3', SEQ ID NO: 3) or IL13Rα2 [10] were obtained from Sigma-Aldrich. siRNAs, as well as the vectors encoding for wild type or mutated IL13Rα2 were transfected with JetPrime (Polyplus Transfection).

Western Blot

Western blot assays were done as previously described [20].

Immunoprecipitation and Mass Spectrometry

Immunoprecipitation (IP) assays were done as previously described [20]. For mass spectrometry (MS) analysis, 2 mg of cell lysates were subjected to immunoprecipitation and loaded in SDS-PAGE. Mass spectrometry conditions and analyses were carried out as previously described.

Adhesion, Wound Healing and Invasion Assays

Adhesion, wound healing and invasion assays have been previously reported [21].

MTT assays for proliferation assessment and for survival to oxidative stress.

Proliferation assays have been previously described [21]. To assess cell survival to oxidative stress, $10^4$ cells were seeded per well on 96-well plates and incubated for 24 h in DMEM containing 1% serum in presence of 1 mM $H_2O_2$, followed by 1 h incubation with MTT. Cell viability was determined by $A_{560\ nm}$ and compared with untreated cells.

Flow cytometry, internalization and glucose uptake assays.

Flow cytometry was performed as previously described [20]. For IL13Rα2 internalization assays, cells were starved for 3 h, detached with 2 mM EDTA, incubated 30 min with IL-13 at 37° C., primary and secondary antibodies for 30 min at 4° C. and analyzed in the cytofluorimeter as previously described [21]. For glucose uptake determination, cells were incubated with IL-13 and/or Claramine and subjected to the assays using 2-NBDG glucose uptake assays kit (BioVision) according to manufacturer's instructions. Glucose uptake was quantified in the cytofluorimeter.

In vivo animal experiments.

The Ethics Committee of the Consejo Superior de Investigaciones Cientificas (Madrid, Spain) and the Community of Madrid approved the protocols used for xenograft and intra-spleen injections with mice. For GBM xenografts, NSG mice were subcutaneously inoculated with U251 cells. Then, mice were treated intraperitoneally with 7 doses of Claramine (every three days) starting day 15 after implantation (a total of 2 mg/kg of body weight). The size of subcutaneous tumors was measured every 2 days. After euthanasia, tumors were isolated and the extracts subjected to Western blot analysis to determine IL13Rα2 and PTP1B activation. Liver homing and metastasis experiments in Swiss nude mice have been described [20]. For CRC metastasis, mice were treated with the same dose of Claramine as above. Animals were weighed to study the effects on food intake and tolerance to the treatment.

For intracranial experiments, athymic nude male mice were purchased from Jackson Laboratories. All experiments were approved by the Northwestern University Institutional Animal Care and Use Committee (IACUC). For the intracranial implantation of cannula and tumor cells, 6-8 weeks old female mice were first anesthetized with a ketamine HCl (25 mg/ml)/xylazine (2.5 mg/ml) cocktail. A previously established surgical procedure was utilized in this study with a small variation reflecting the cannula implantation [36]. For that, a custom-made 26 gauge sterile guide cannula (Plastics One, Roanoke, VA) was installed into the brain through a burr hole at 2 mm depth and secured with tissue glue (3M, St Paul, MN). For the glioma PDX cells implantation, a 33-gauge sterile syringe was inserted into the guide cannula at 3 mm depth following by infusion of 2.5 μl of $10^5$ GBM12 cells. The skin incision was closed with surgical glue around the implantation site. The extracranial end of the cannula was then covered with a 33-gauge protection dummy cannula. The surgical procedure was followed with a standard post-surgery care according to the approved protocol. The intracranial injection of Claramine through cannula was done in 4 fractions for a total 4-8 mg/kg starting day 7 after tumor implantation and every 3 days after that. For systemic treatment, Claramine was delivered intravenously in 4 fractions for a total 8, 15 or 30 mg/kg starting day 7 after tumor implantation and every 3 days after that. Sterile 0.9% saline solution served as a negative control in all experiments.

In silico expression and prognostic studies.

The GSE17538 database, which contains 244 tumor samples with clinicopathological data, was used for the prognostic study in CRC. Data were normalized using Bioconductor's Affymetrix package. The prognostic value of PTP1B expression level was assessed using Kaplan-Meier survival curves, where negative and positive z-scoreswere considered as low and high expression, respectively. For glioma tumors, PTP1B association with prognosis was evaluated using the REMBRANDT dataset (containing 329 samples) using the median as a threshold to divide into low and high expression populations. For ovarian cancer, PTP1B association with survival was assessed using the GEPIA2 dataset (gepia.cancer-pku.cn) containing 468 ovarian cancer samples. They were analyzed by considering as threshold for high PTP1B expression the 40% most positive samples.

Statistical analyses.

At least three replicates were done for each experiment. Data were analyzed by one-way ANOVA followed by Tukey-Kramer multiple comparison test. The significance of the difference for survival curves was estimated with the log-rank test. In all analyses, the minimum acceptable level of significance was $p<0.05$.

Example 1: PTP1B Associates with IL13Rα2 in Cancer Cells

Figure 1B:
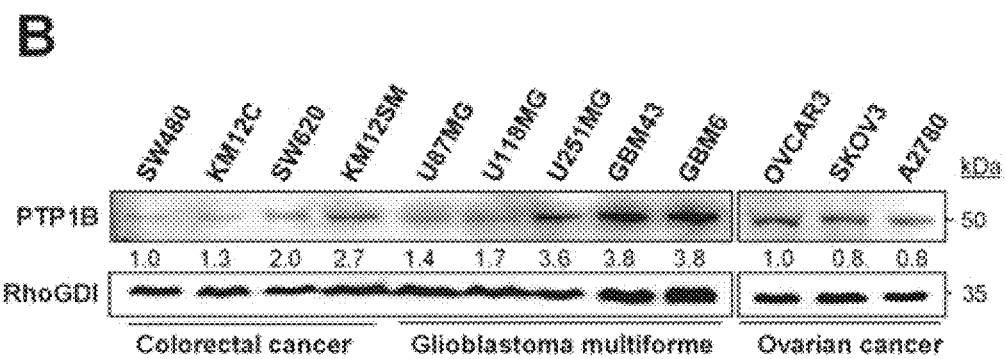
Figure 1C:
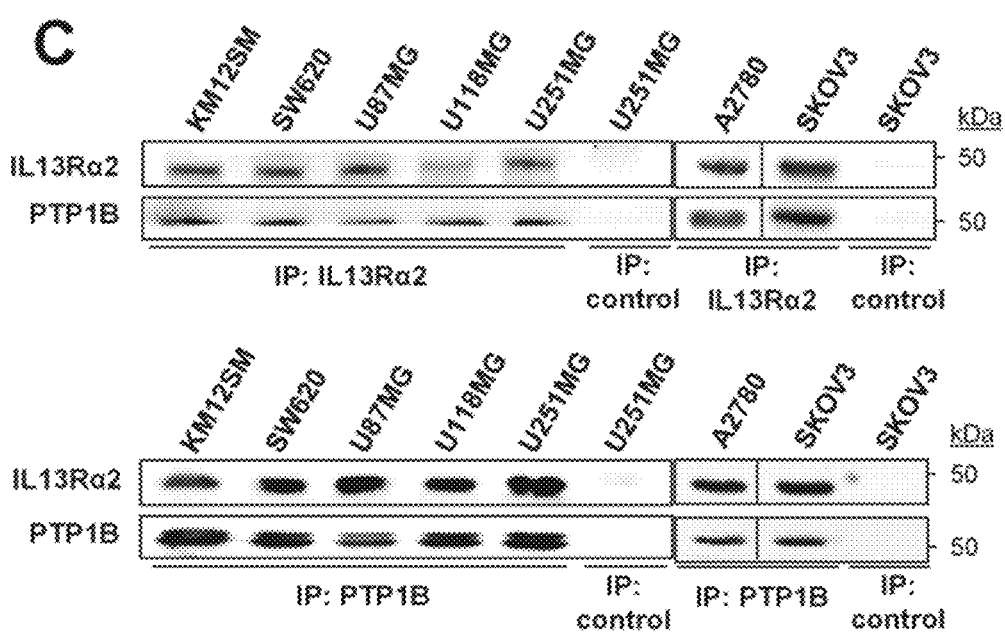

To characterize the protein interaction network of IL13Rα2, whole-cell lysates of the human GBM cell line U251 were immunoprecipitated and analyzed by mass spectrometry. Eleven proteins were found to be (i) specifically associated with IL13Rα2 after removing those proteins immunoprecipitated with a control antibody or (ii) involved in non-specific protein-binding functions (i.e. chaperons and ribosomal proteins). A schematic representation of the interacting proteins and their tentative location is depicted in FIG. 1A. Based on the number of identified peptides, the phosphatase PTP1B was selected as the most relevant IL13Rα2 interaction partner. PTP1B expression was analyzed in a panel of four IL13Rα2 positive CRC cell lines [10], three GBM cell lines, two GBM patient-derived xenografts (PDXs) and three OC cell lines (FIG. 1B). Although all the cells expressed PTP1B, the highest level of PTP1B protein was found in the GBM PDXs. The association of PTP1B with IL13Rα2 was confirmed in the different cell lines by co-IP with either PTP1B or IL13Rα2-specific antibodies followed by Western blot detection (FIG. 1C).

Figure 1D:
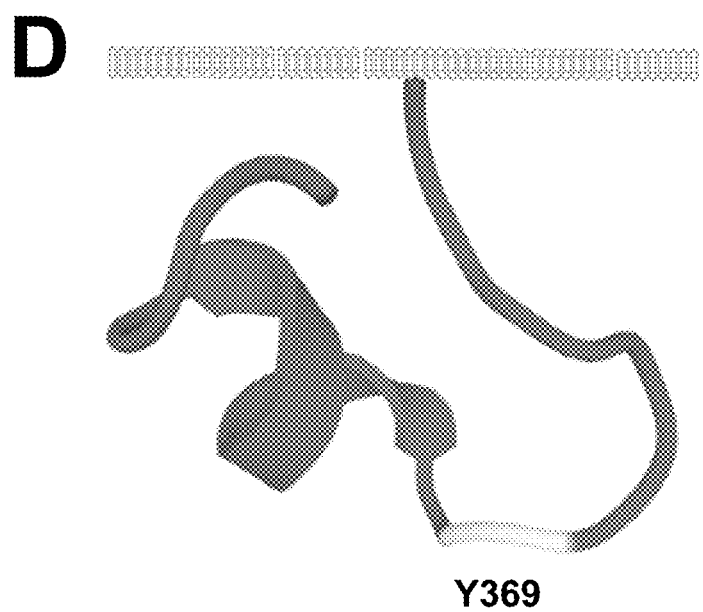
Figure 1E:
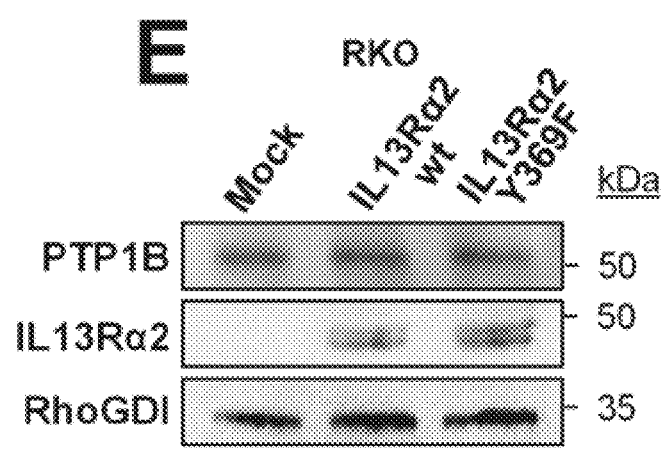
Figure 1F:
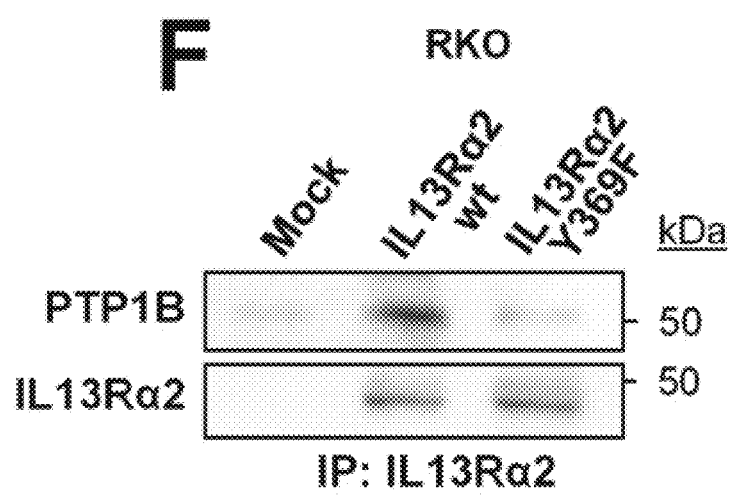
Figure 1G:
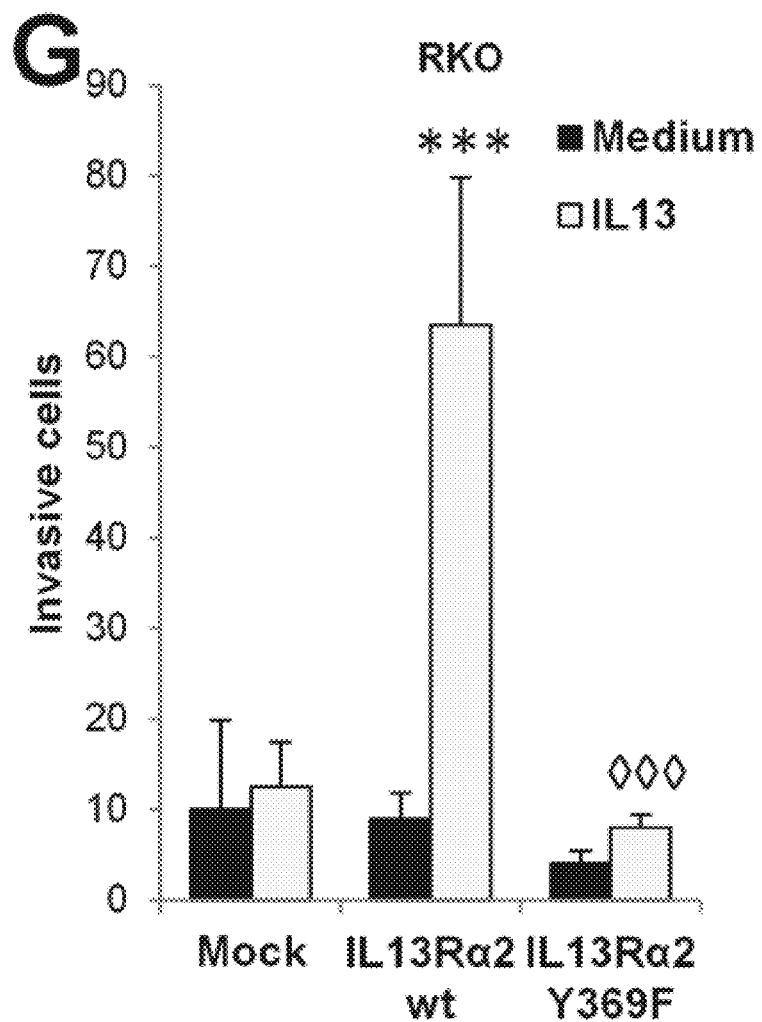

It was hypothesized that Tyr369 of the IL13Rα2 cytoplasmic tail could be the anchor point for PTP1B (FIG. 1D). To assess this hypothesis, mutant Tyr369Phe and wild type IL13Rα2 were transformed into RKO CRC cells, which do not express IL13Rα2. The expression of wild-type and mutant IL13Rα2, as well as the endogenous expression of PTP1B in RKO cells, was verified by Western blot (FIG. 1E). PTP1B was found to be exclusively associated with the wild-type IL13Rα2, but not with the mutant form of Tyr369 (FIG. 1F). Moreover, RKO cells containing the mutant Tyr369Phe showed a clear inhibition of the invasive properties (FIG. 1G). Taken together, these results support a role for the phosphorylated Tyr369 in the pro-invasive effects of IL13Rα2 through PTP1B binding.

Figure 2A:
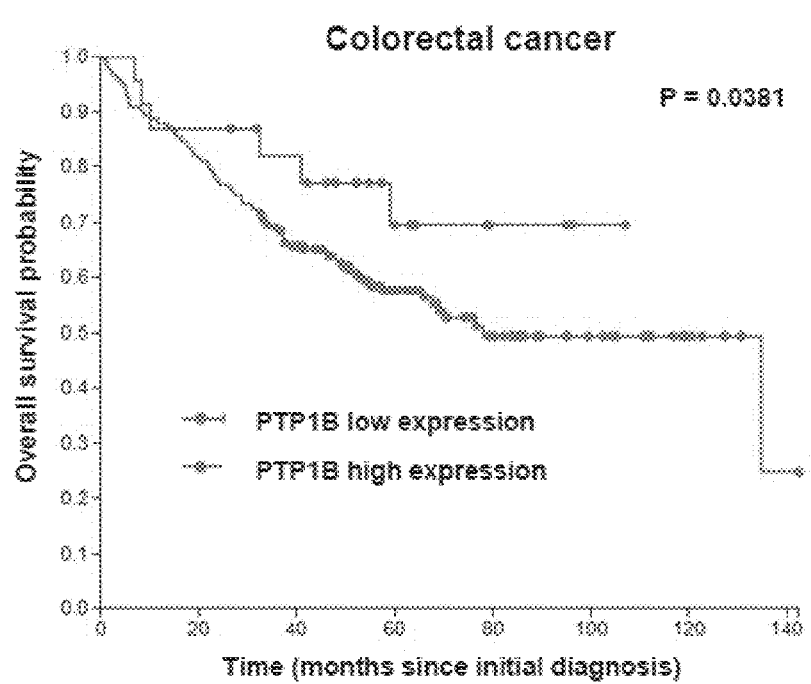
FIGS. 2A-2D show prognostic value of PTP1B in cancer patients. Kaplan-Meier survival analysis is shown in FIG. 2A.
Figure 2B:
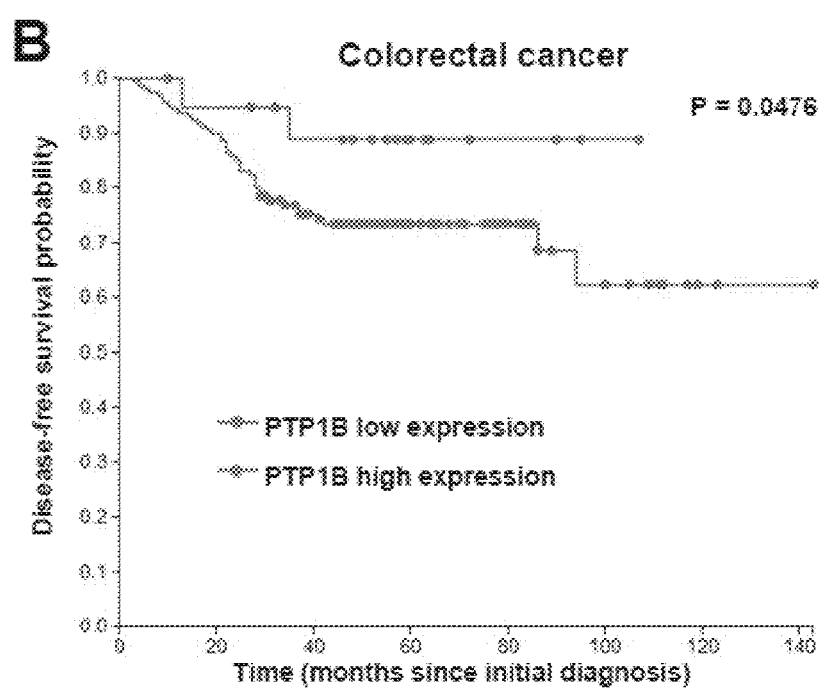
Figure 2C:
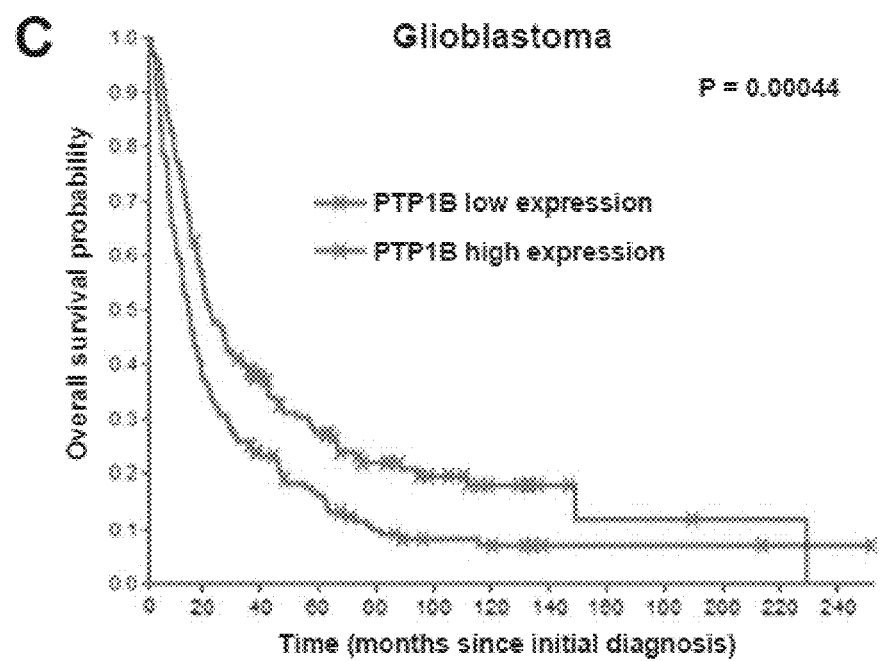
Figure 2D:
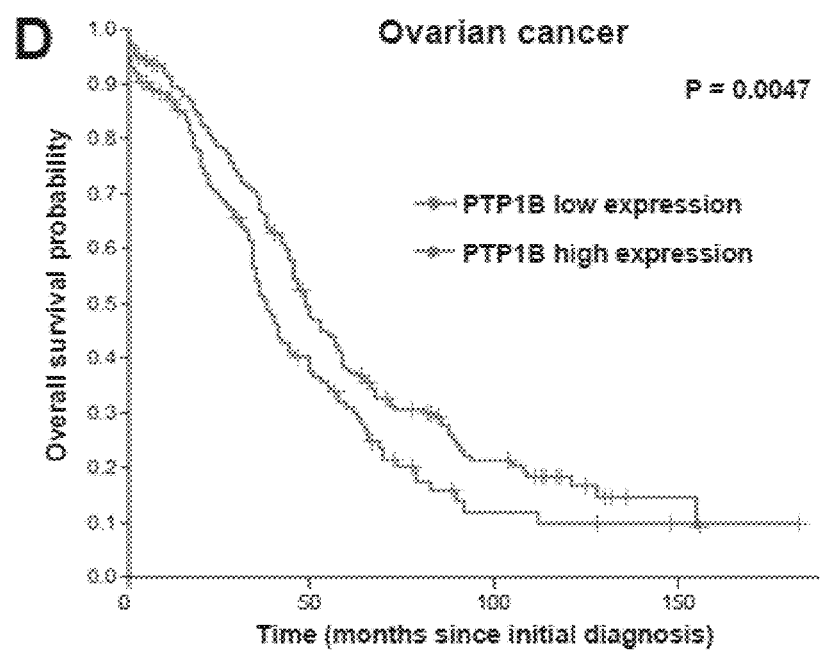

Example 2: PTP1B Overexpression is Associated with a Lower Overall Survival of Patients To study the clinical relevance of PTP1B, "in silico" studies of PTP1B expression were performed. For human colorectal cancer, in silico analysis of the GSE17538 dataset was performed. Although the z-score for PTP1B expression was not distributed in a Gaussian fashion, 90% of the tumor samples expressed significantly higher levels of PTP1B. Then, a significantly negative correlation was found between PTP1B expression levels and overall (FIG. 2A) or disease-free survival (FIG. 2B) for colorectal cancer patients. To investigate the relevance of PTP1B expression in glioma patients, the REMBRANDT data repository was used. Using the median as a threshold, a significantly reduced overall survival of GBM patients with high PTP1B expression was found (FIG. 2C). PTP1B expression in OC was analyzed using the GEPIA2 database. Results indicated an association of high PTP1B expression with lower overall survival (FIG. 2D). However, in silico analysis did not show a significant correlation between PTP1B and IL13Rα2 expression (data not shown). Collectively, these results support an association between increased PTP1B expression and poorer patient outcome in the three types of cancer.

Figure 3:
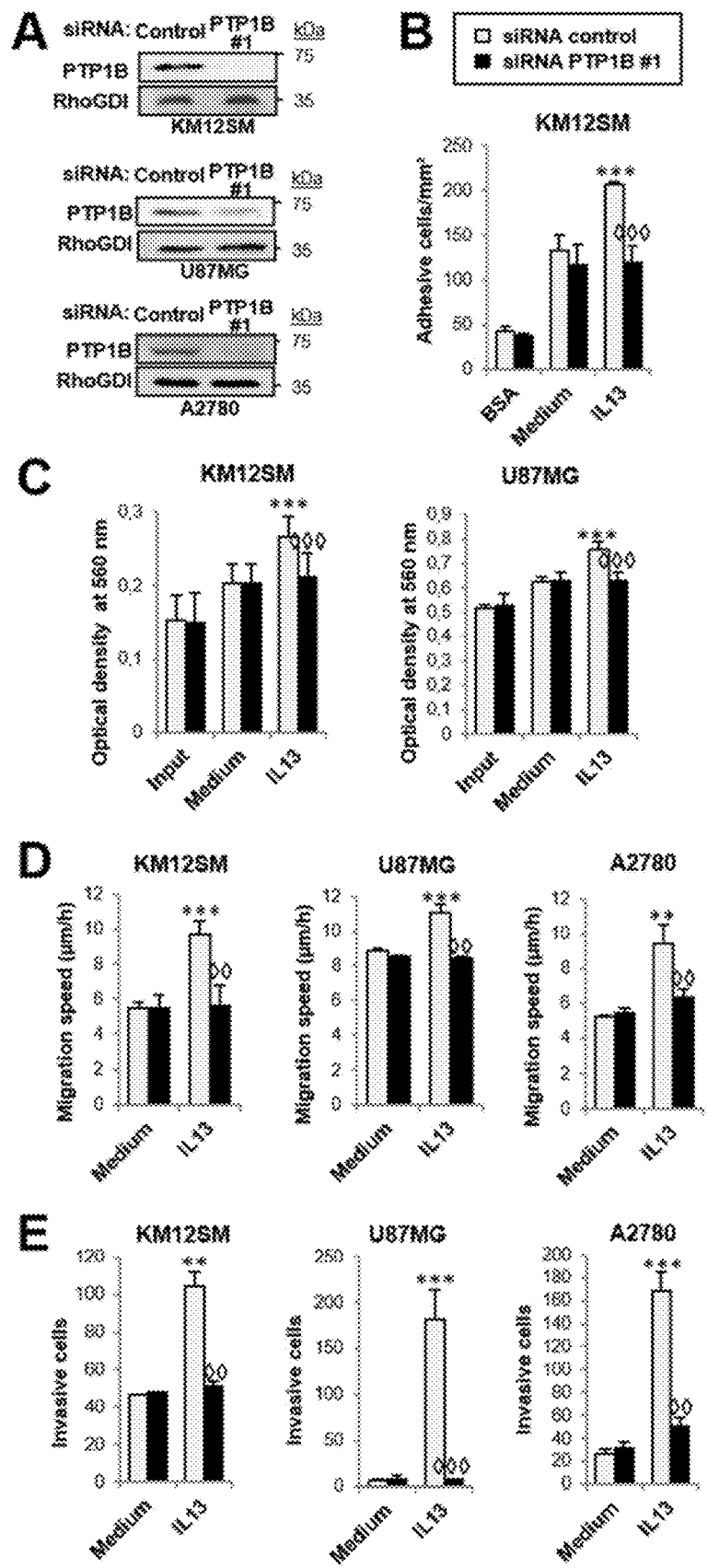
FIG. 3. Shows how PTP1B mediates IL-13-triggered cell adhesion, migration, invasion and proliferation in cancer cells. U87MG, KM12SM, and A2780 cells were transfected with control or PTP1B siRNA #1. A) PTP1B silencing was verified 48 h after transfection by Western blot. B) Colorectal cancer transfectants were subjected to cell adhesion. C) Glioblastoma and colorectal cancer transfectants were subjected to MTT. Then, the three cancer transfectants were subjected to D) migration and E) invasion assays. All assays were done in the presence or absence of IL-13. Cell adhesion/migration/invasion/optical density was significantly increased by addition of IL-13 (*, $p<0.05$; , $p<0.01$; *, $p<0.001$) and declined after PTP1B silencing (0, $p<0.05$; 00, $p<0.01$; 000, $p<0.001$).

Example 3: PTP1B Mediates IL13-Induced Cancer Cell Proliferation, Migration, Invasion and Survival To investigate the activity of PTP1B in the pro-invasive and metastatic processes induced by IL-13 in cancer cells, PTP1B-silenced KM12SM/SW620 CRC, U118/U87 GBM and A2780/SKOV3 OC cells were prepared using two different siRNAs (FIG. 3A). PTP1B-silenced and control cells were investigated for cell adhesion, proliferation, migration, and invasion in the presence or absence of IL-13. Experiments were performed in absence of serum, except proliferation (0.5% serum). After IL-13 addition, only CRC cells showed an apparent increase in cell adhesion that was inhibited by PTP1B silencing (FIG. 3B). IL-13 effect on proliferation increase was restricted to CRC and GBM with no effect in OC cells and was inhibited after PTP1B silencing (FIG. 3C). The IL-13-promoted migration and invasion were decreased by PTP1B silencing in all tested CRC, OC and GBM cell lines (FIG. 3D-E). In addition, as PTP1B has been involved in the activation of the PI3K/AKT pathway, the effect of IL-13 and PTP1B on cell survival was tested. The presence of IL-13 improved the survival of cells subjected to oxidative stress. This survival increase was abolished after PTP1B silencing with two different siRNAs. Collectively, these results support that IL13-induced proliferation, migration, invasion and survival were mediated through PTP1B.

Figure 4A:
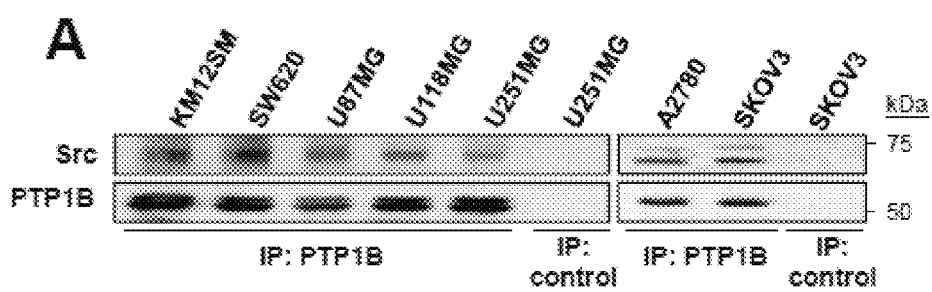
FIGS. 4A-4C. show IL-13 signaling is mediated by PTP1B via Src activation.
Figure 4B:
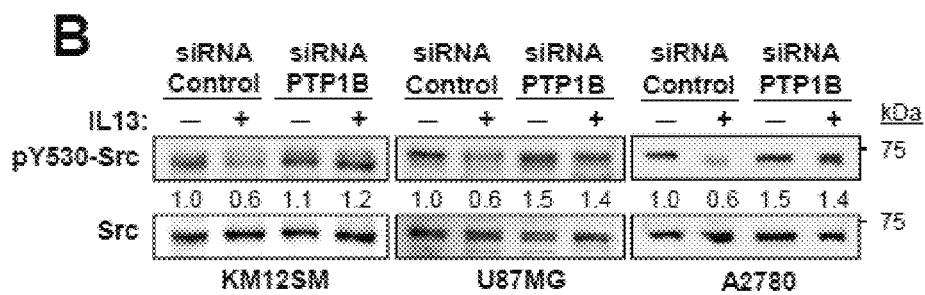
Figure 4C:
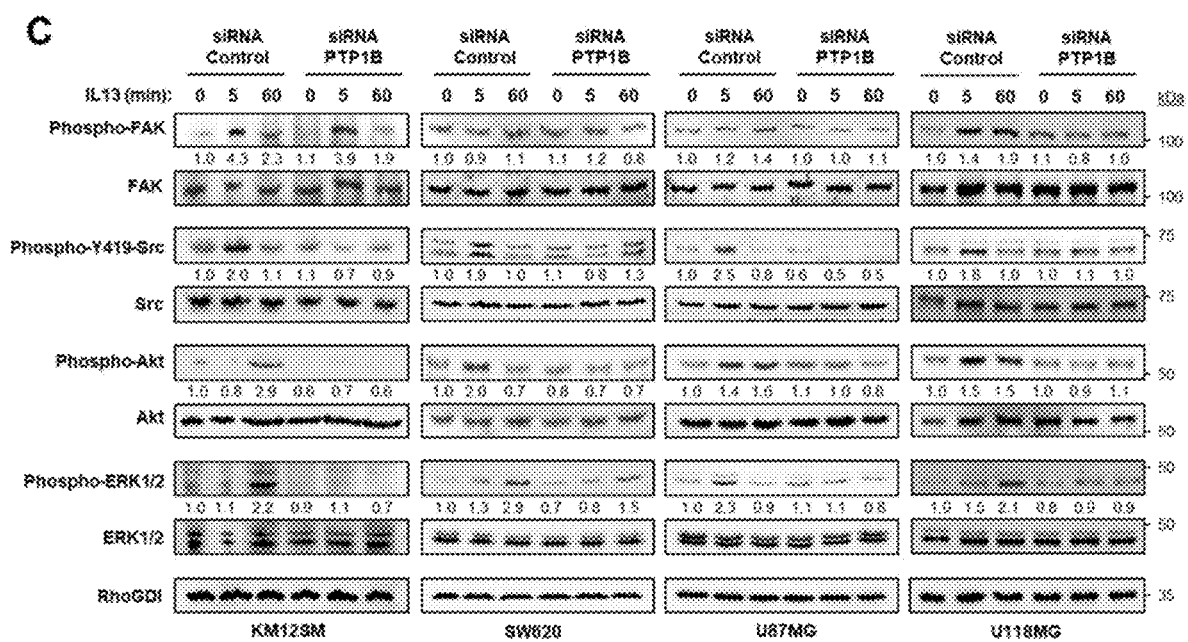

Example 4: IL-13 Signaling Through IL13Rα2 Requires PTP1B for Src Activation First, the presence of Src in the PTP1B immunoprecipitates of the three types of cancer was confirmed (FIG. 4A). Then, the phosphorylation of Src $Tyr_{530}$ in PTP1B-silenced cells was tested. Whereas addition of IL-13 reduced the phosphorylation of Src $Tyr_{530}$ in control cells, the phosphorylation levels in PTP1B-silenced cells remained constant (FIG. 4B). As pSrc $Tyr_{530}$ prevents the phosphorylation of pSrc $Tyr_{419}$, the effect of knocking down PTP1B on Src $Tyr_{419}$ phosphorylation in the three tested cell lines was investigated on FAK, AKT and ERK1/2 activation at different times. pSrc $Tyr_{419}$ activation was an early event (5 min) that was suppressed by KD PTP1B and the consequent phosphorylation of Src $Tyr_{530}$ (FIG. 4C). FAK phosphorylation was not affected by PTP1B silencing, except in U118 GBM cells (FIG. 4C). The increase of AKT and ERK1/2 phosphorylation occurred between 5-60 min in the tested cell lines and was also decreased after PTP1B silencing (FIG. 4C). In summary, PTP1B-silencing inhibited the Src/AKT/ERKpathway activation induced by IL-13 binding to IL13Rα2 in cancer cells.

Figure 5:
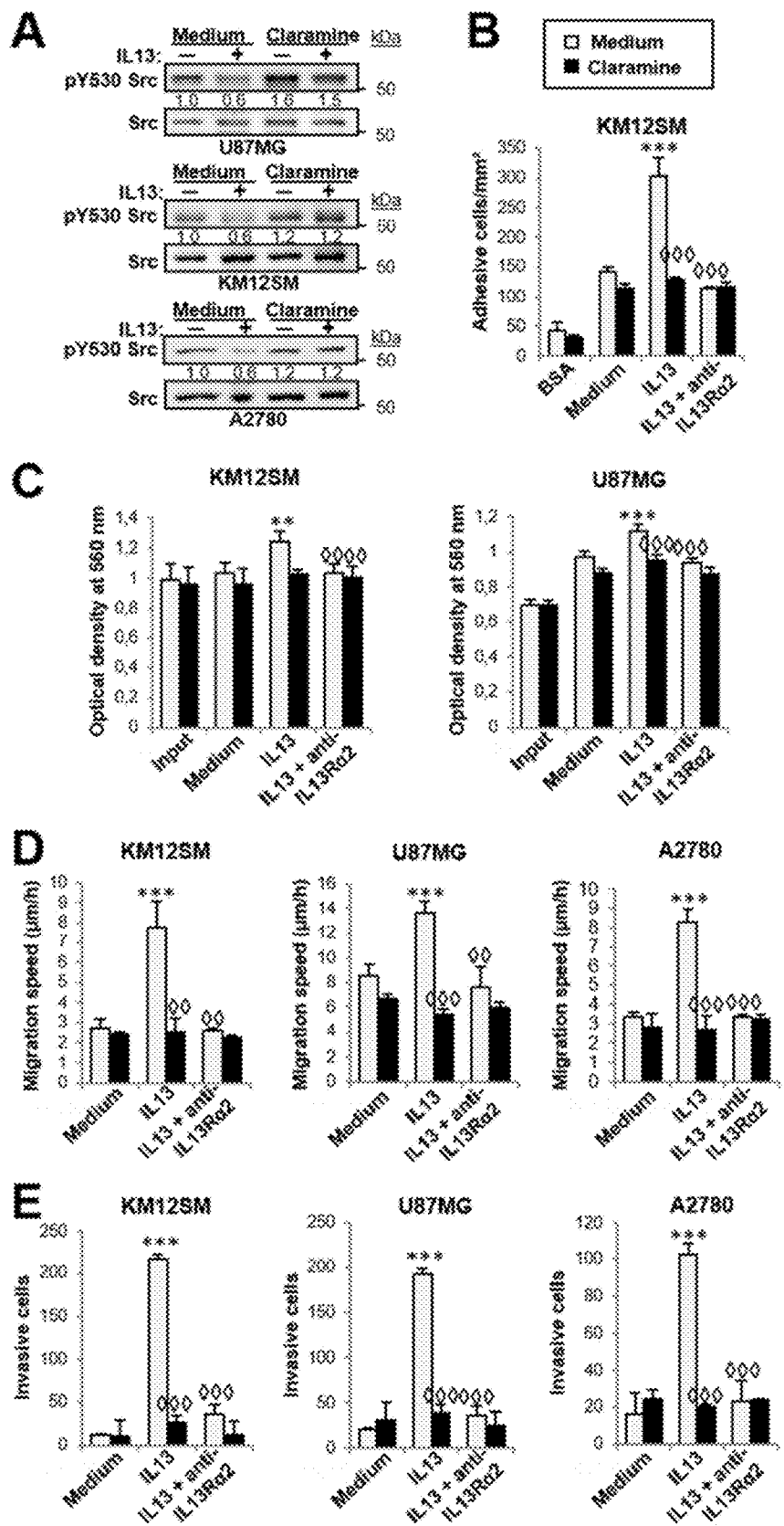
FIG. 5. Shows how Claramine inhibits cell adhesion, migration, invasion and proliferation triggered by IL-13. A) U87MG, KM12SM and A2780 cells, treated with or without Claramine, were exposed to IL-13, lysed and the extracts analyzed by Western blotto detect $pSrcY_{530}$ and total Src. B) KM12SM cells were subjected to cell adhesion. C) KM12SM and U87MG cells were subjected to MTT assays. The three cell lines were subjected to D) migration and E) invasion assays. All the experiments were done in the presence or absence of IL-13, Claramine and/or anti-IL13Rα2 blocking antibodies. Cell adhesion/migration/invasion and proliferation were significantly increased by addition of IL-13 (, $p<0.01$; *, $p<0.001$) and inhibited by treatment with Claramine or the blocking antibody (00, $p<0.01$; 000, $p<0.001$).

Example 5: Claramine, a PTP1B Inhibitor, Reduces Cell Migration, Invasion, Proliferation and Survival Next, the effect of the PTP1B inhibitor Claramine on the pro-invasive effects of IL-13 was investigated. First, the cellular toxicity of Claramine was studied at different doses. Claramine at 5 µM caused around 50% decrease in cell survival, but had no effect at 2 µM, which was used in the remaining experiments (data not shown). Treatment with 2 µM Claramine preserved the phosphorylation of Src $Tyr_{530}$ in IL13-treated U87MG, KM12SM, and A2780 cells (FIG. 5A). The effects of Claramine on cell adhesion, migration, invasion, and, to a minor extent, proliferation mimicked the effects of PTP1B silencing in the three types of cancer cells (FIG. 5 B-E). In colorectal cancer, treatment with Claramine abolished IL-13-induced cell adhesion to Matrigel at a similar extent to the use of a blocking IL13Rα2 antibody (clone 47) [34], suggesting that both treatments are likely blocking the same pathway (FIG. 5B). Proliferation was also inhibited by Claramine in KM12SM and U87MG (FIG. 5C). The most significant effects of Claramine were observed in its capacity to inhibit cell migration and invasion in the three types of cancer, in a similar way to the IL13Rα2 antibody (FIG. 5D-E). A significant reduction in IL-13 promoted cell survival after treatment with Claramine was also noticed (data not shown). Together, these results support the functional relevance of PTP1B inhibitors for blocking the IL13Rα2 signaling pathway.

Example 6: Effect of Claramine on EGF, IRS-1 and Glucose Homeostasis

Figure 6:
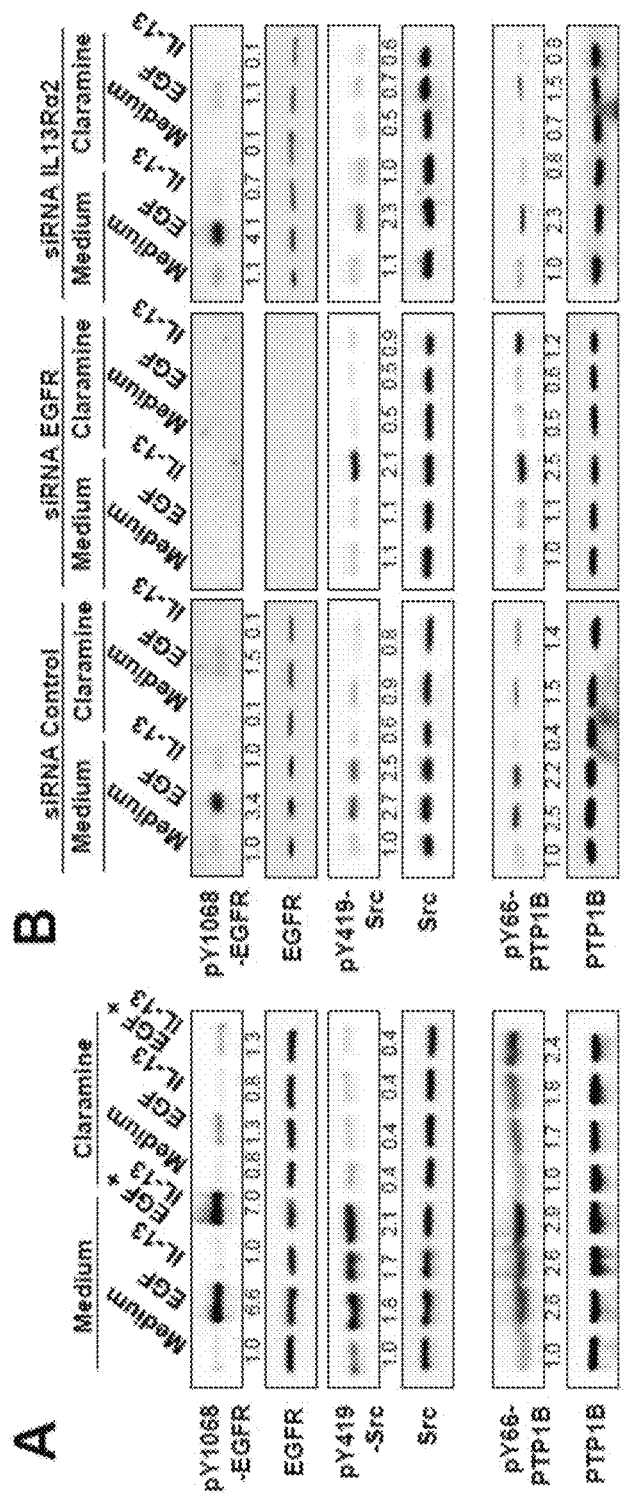
FIG. 6. Shows the effect of Claramine on EGF and IL-13 signaling in GBM cells. (A) U251 cells were treated with EGF, IL-13 or both, with or without Claramine. Cell extracts were analyzed by western blot to detect $pEGFR\ Y_{1068}$, $pPTP1B\ Y_{66}$, and $pSrc\ Y_{419}$. B) U251 cells silenced for EGFR, IL13Rα2 or control cellswere treated with EGF or IL-13 in the presence or absence of Claramine. Cells were lysed and whole extracts were analyzed by western blot to detect $pEGFR\ Y_{1068}$, $pPTP1B\ Y_{66}$ and $pSrc\ Y_{419}$.

EGFR is a substrate of PTP1B and might cooperate with IL13Rα2 in GBM invasion [35]. To determine whether PTP1B participates in the modulation of the EGFR pathway besides the IL13Rα2, the effect of Claramine on EGF and IL-13 signaling in GBM was investigated. In U251 GBM cells, phospho-EGFR $Tyr_{1068}$ was only activated by EGF (FIG. 6A), while Src $Tyr_{419}$ phosphorylation was indistinctly triggered by EGF or IL-13. PTP1B $Tyr_{66}$ was also phosphorylated by EGF and IL-13, indicating the participation of PTP1B in both pathways. Claramine inhibited the activation of EGFR and Src by EGF and IL-13, blocking the phosphatase active site independently of the PTP1B activation (FIG. 6A). The combination of both EGF and IL-13 retained a significant PTP1B $Tyr_{66}$ phosphorylation suggesting an additive effect. However, EGFR-silencing did not reduce PTP1B and Src activation mediated by IL-13. Similarly, IL13Rα2-silencing did not inhibit EGFR/PTP1B/Src activation by EGF. In contrast, Claramine suppressed both EGFR and Src activation (FIG. 6B). Taken together, these data confirm that inhibition of PTP1B by Claramine might be an efficient strategy to block not only IL13 but EGF-promoted Src activation in GBM cells, increasing the potential therapeutic value of PTP1B inhibitors.

As PTP1B silencing or Claramine treatment might modulate glucose and energy homeostasis including insulin signaling, the effect of IL-13 on the glucose uptake and insulin signaling was also investigated. IL-13 increased the glucose uptake in GMB cells but not in CRC cells (data not shown). However, the use of Claramine did not inhibit this uptake in GBM cells. The phosphorylation of insulin receptor substrate 1 (IRS-1) in CRC and GBM cells treated with IL-13 and Claramine was then studied. A strong phosphorylation of IRS-1 in U251 cells treated with IL-13 was found. In contrast, phosphorylation of IRS-1 in KM12SM cells was much weaker, without differences after IL-13 addition. However, the inhibition of PTPB1 with Claramine did not affect IRS-1 phosphorylation in none of the cell lines. Together, these studies support that Claramine effect on tumor cells seems to be independent of the glucose homeostasis.

Figure 7A:
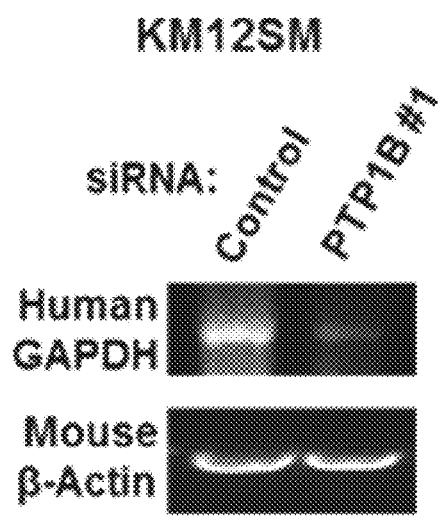
FIGS. 7A-7E show PTP1B inhibition increases survival in CRC and glioblastoma mouse models.
Figure 7B:
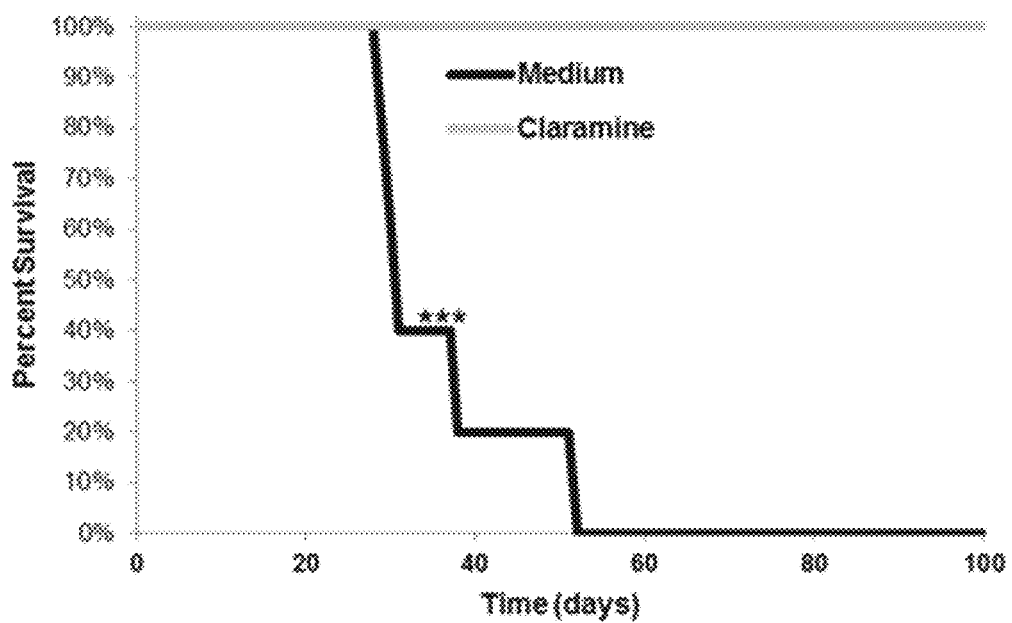

Example 7: Claramine Increases Survival to Metastasis and Invasion in CRC and GBM Mouse Models Finally, the in vivo effects of PTP1B silencing or inhibition in colorectal cancer and glioblastoma mouse models were investigated. Given the high homology between murine and human IL-13, it was hypothesized that it was unnecessary to treat the mice with exogenous human IL-13 (11). Fora further confirmation, human and murine IL-13 were compared in an invasion experiment. Both IL-13 promoted a similar pro-invasive capacity on human cancer cells (data not shown). Then, the effect of PTP1B silencing on the capacity for liver homing of KM12SM cells inoculated in the spleen of nude mice was examined. As a surrogate marker for homing, human GAPDH was detected in the livers of mice inoculated with control cells but not in those inoculated with PTP1B-silenced cells (FIG. 7A). Then, the effects of Claramine on mice survival in colorectal cancer metastasis were investigated. Forty-eight h after spleen inoculation with CRC cells, mice were treated intraperitoneally (i.p.) with Claramine for two weeks on alternate days, with a total dose of 49 µg/mouse. Treated mice % ere sacrificed at day 100 post-inoculation without symptoms of the disease, presence of metastatic nodes or weight loss. Kaplan-Meier survival curves showed that Claramine caused complete protection against liver metastases in the treated mice (FIG. 7B).

Figure 7C:
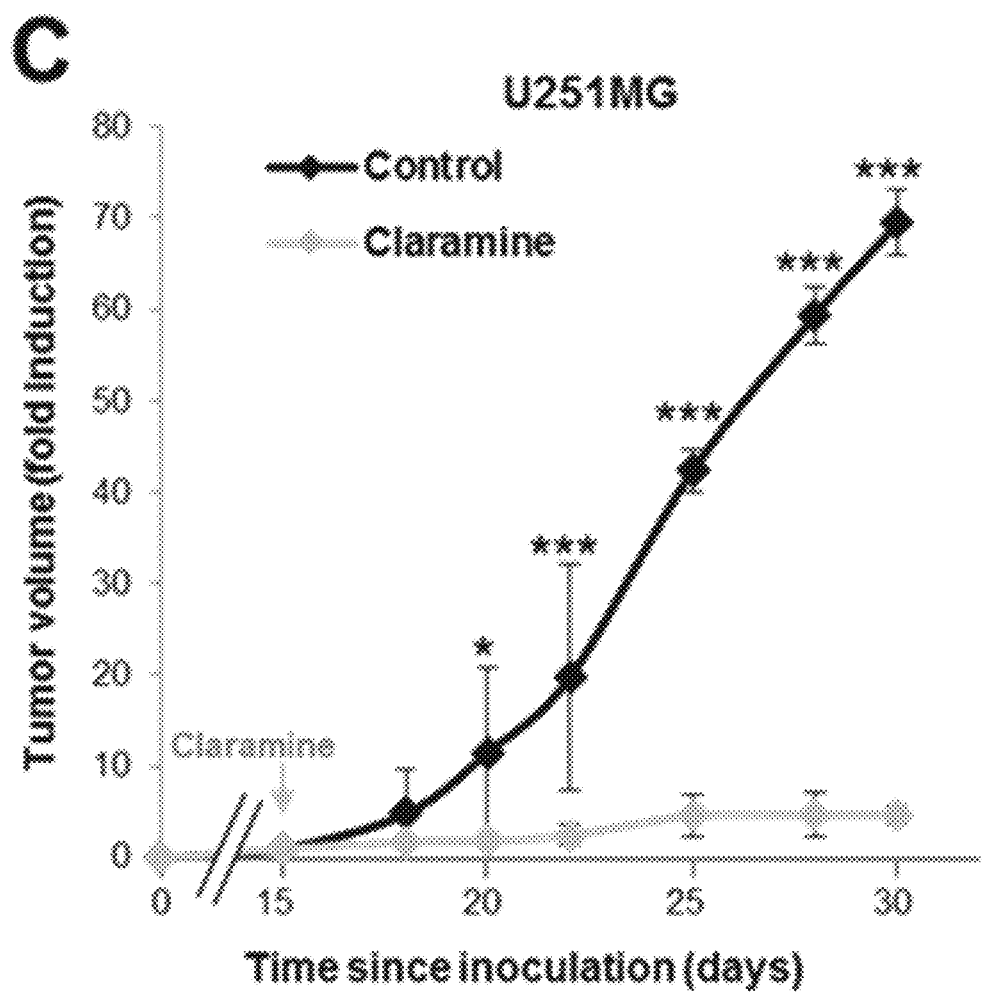
Figure 7D:
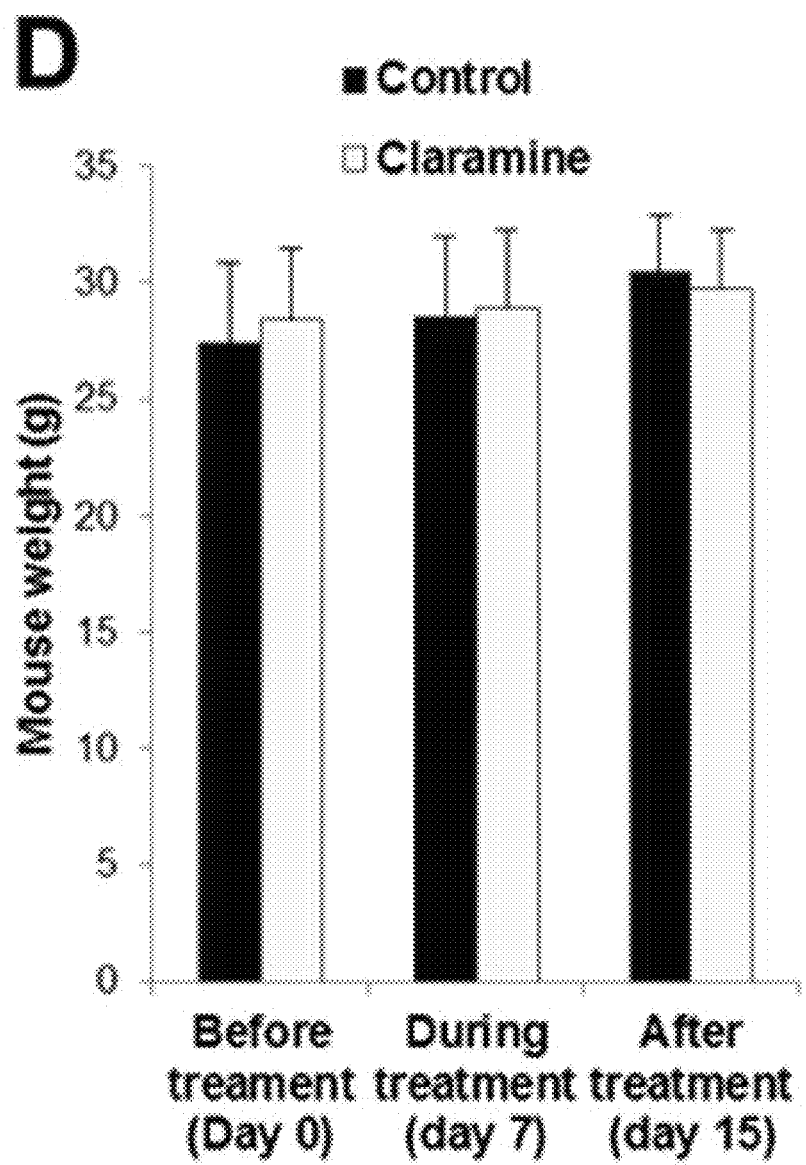

Next, the in vivo effect of Claramine on GBM tumor growth and intracranial inoculation was investigated. First, mice were subcutaneously inoculated with U251 cells and xenografts were allowed to grow for 15 days before starting i.p. treatment with Claramine (FIG. 7C). Tumors in treated mice stop growing for the duration of the treatment when compared with non-treated mice. No Claramine toxicity was observed in the treated animal as indicated by the constant weight of the animals (FIG. 7D). In addition, the involvement of IL13Rα2 and PTP1B in the tumor growth was studied using xenograft tissues. A significant increase of PTP1B phosphorylation (3-5 times) in vivo compared to cells in culture was found. Treatment with Claramine provoked a moderate inhibition in the phosphorylation of PTP1B as previously observed in cultured cells (FIG. 6A). An increased expression of IL13Rα2 in the xenografts was also noticed. These results indicate a correlation between increased IL13Rα2 expression and PTP1B activation associated to tumor growth.

Figure 7E:
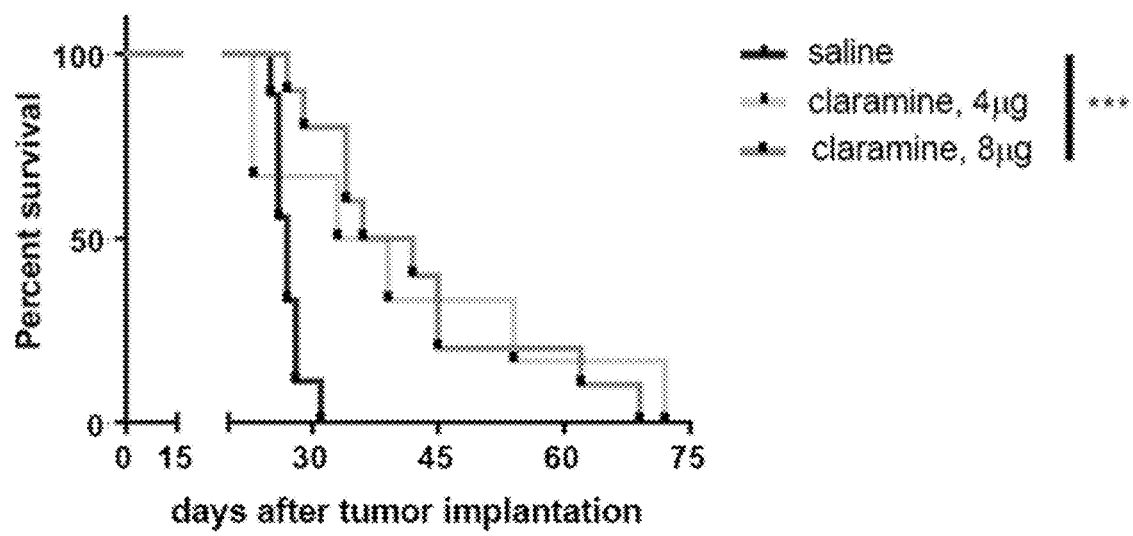

Finally, an intracranial model of GBM using the GBM12 PDX that expresses high amounts of IL13Rα2 was tested. Tumors were implanted intracranially for seven days before starting the treatment with four doses of Claramine for a total of 4 mg/kg or 8 mg/kg (FIG. 7E). The median survival for the treated mice increased up to 36-39 days from 27 days of the control mice. Treated mice survived up to 70-72 days post-inoculation and Kaplan-Meier analysis showed a statistically significant difference in survival between treated and control groups ($p<0.001$). In summary, these data demonstrate the efficacy of Claramine for improving glioblastoma and colorectal cancer survival in mouse models.

CONCLUSION

The association between IL13Rα2 and the tyrosine phosphatase PTP1B and its effect on signaling in different cancer types is proved herein, paving the way to the therapeutic use of PTP1B inhibitors.

Claramine, a PTP1B inhibitor, has been shown to abolish the IL-13 pro-invasive and pro-metastatic effects and to cause a complete inhibition of CRC liver metastasis in Swiss nude mice, the regression of GBM xenografts and a considerable increase of mice survival after intracranial inoculation of PDX GBM cells. Thus, PTP1B inhibition is a promising strategy for cancers overexpressing IL13Rα2, including but not limited to advanced colorectal, ovarian, and glioblastoma.

REFERENCES

1. Debinski, W.; Gibo, D. M., Molecular expression analysis of restrictive receptor for interleukin 13, a brain tumor-associated cancer/testis antigen. *Mol Med* 2000, 6, (5), 440-9.
2. Debinski, W.; Gibo, D. M., et al., Receptor for interleukin 13 is a marker and therapeutic target for human high-grade gliomas. *Clin Cancer Res* 1999, 5, (5), 985-90.
3. Fujisawa, T.; Joshi, B., et al., A novel role of interleukin-13 receptor alpha2 in pancreatic cancer invasion and metastasis. *Cancer Res* 2009, 69, (22), 8678-85.
4. Bernard, J.; Treton, D., et al., Expression of interleukin 13 receptor in glioma and renal cell carcinoma: IL13Ralpha2 as a decoy receptor for IL13. *Lab Invest* 2001, 81, (9), 1223-31.
5. Beard, R. E.; Abate-Daga, D., et al., Gene expression profiling using nanostring digital RNA counting to identify potential target antigens for melanoma immunotherapy. *Clin Cancer Res* 2013, 19, (18), 4941-50.
6. Takenouchi, M.; Hirai, S., et al., Epigenetic modulation enhances the therapeutic effect of anti-IL-13R(alpha)2 antibody in human mesothelioma xenografts. *Clin Cancer Res* 2011, 17, (9), 2819-29.
7. Kawakami, M.; Kawakami, K., et al., Interleukin-13 receptor alpha2 chain in human head and neck cancer serves as a unique diagnostic marker. *Clin Cancer Res* 2003, 9, (17), 6381-8.
8. Kioi, M.; Kawakami, M., et al., Interleukin-13 receptor alpha2 chain: a potential biomarker and molecular target for ovarian cancer therapy. *Cancer* 2006, 107, (6), 1407-18.
9. Hallett, M. A.; Venmar, K. T.; Fingleton, B., Cytokine stimulation of epithelial cancer cells: the similar and divergent functions of IL-4 and IL-13. *Cancer Res* 2012, 72, (24), 6338-43.
10. Barderas, R.; Bartolome, R. A., et al., High expression of IL-13 receptor alpha2 in colorectal cancer is associated with invasion, liver metastasis, and poor prognosis. *Cancer Res* 2012, 72, (11), 2780-90.
11. Fujisawa, T.; Joshi, B. H.; Puri, R. K., IL-13 regulates cancer invasion and metastasis through IL-13Ralpha2 via ERK/AP-1 pathway in mouse model of human ovarian cancer. *Int J Cancer* 2012, 131, (2), 344-56.
12. Lal, A.; Glazer, C. A., et al., Mutant epidermal growth factor receptor up-regulates molecular effectors of tumor invasion. *Cancer Res* 2002, 62, (12), 3335-9.
13. Brown, C. E.; Warden, C. D., et al., Glioma IL13Ralpha2 is associated with mesenchymal signature gene expression and poor patient prognosis. *PLoS One* 2013, 8, (10), e77769.
14. Kawakami, M.; Kawakami, K., et al., Analysis of interleukin-13 receptor alpha2 expression in human pediatric brain tumors. *Cancer* 2004, 101, (5), 1036-42.
15. Jarboe, J. S.; Johnson, K. R., et al., Expression of interleukin-13 receptor alpha2 in glioblastoma multiforme: implications for targeted therapies. *Cancer Res* 2007, 67, (17), 7983-6.
16. Stupp, R.; Taillibert, S., et al., Effect of Tumor-Treating Fields Plus Maintenance Temozolomide vs Maintenance Temozolomide Alone on Survival in Patients With Glioblastoma: A Randomized Clinical Trial. *JAMA* 2017, 318, (23), 2306-2316.
17. Thaci, B.; Brown, C. E., et al., Significance of interleukin-13 receptor alpha 2-targeted glioblastoma therapy. *Neuro Oncol* 2014, 16, (10), 1304-12.
18. Fichtner-Feigl, S.; Strober, W., et al., IL-13 signaling through the IL-13alpha2 receptor is involved in induction of TGF-beta1 production and fibrosis. *Nat Med* 2006, 12, (1), 99-106.
19. Bhardwaj, R.; Suzuki, A., et al., Identification of a novel role of IL-13Ralpha2 in human Glioblastoma multiforme: interleukin-13 mediates signal transduction through AP-1 pathway. *J Transl Med* 2018, 16, (1), 369.
20. Bartolome, R. A.; Garcia-Palmero, I., et al., IL13 Receptor alpha2 Signaling Requires a Scaffold Protein, FAM120A, to Activate the FAK and PI3K Pathways in Colon Cancer Metastasis. *Cancer Res* 2015, 75, (12), 2434-44.
21. Bartolome, R. A.; Jaen, M.; Casal, J. I., An IL13Ralpha2 peptide exhibits therapeutic activity against metastatic colorectal cancer. *Br J Cancer* 2018, 119, (8), 940-949.
22. Lessard, L.; Stuible, M.; Tremblay, M. L., The two faces of PTP1B in cancer. *Biochim Biophys Acta* 2010, 1804, (3), 613-9.
23. Chen, Q.; Li, Y., et al., Overexpression of PTP1B in human colorectal cancer and its association with tumor progression and prognosis. *J Mol Histol* 2014, 45, (2), 153-9.
24. Hoekstra, E.; Das, A. M., et al., Increased PTP1B expression and phosphatase activity in colorectal cancer results in a more invasive phenotype and worse patient outcome. *Oncotarget* 2016, 7, (16), 21922-38.
25. Lessard, L.; Labbe, D. P., et al., PTP1B is an androgen receptor-regulated phosphatase that promotes the progression of prostate cancer. *Cancer Res* 2012, 72, (6), 1529-37.
26. Wiener, J. R.; Kerns, B. J., et al., Overexpression of the protein tyrosine phosphatase PTP1B in human breast cancer: association with p185c-erbB-2 protein expression. *J Natl Cancer Inst* 1994, 86, (5), 372-8.
27. Wiener, J. R.; Hurteau, J. A., et al., Overexpression of the tyrosine phosphatase PTP1B is associated with human ovarian carcinomas. *Am J Obstet Gynecol* 1994, 170, (4), 1177-83.
28. Wang, J.; Liu, B., et al., PTP1B expression contributes to gastric cancer progression. *Med Oncol* 2012, 29, (2), 948-56.
29. Wang, N.; She, J., et al., Frequent amplification of PTP1B is associated with poor survival of gastric cancer patients. *Cell Cycle* 2015, 14, (5), 732-43.
30. Bjorge, J. D.; Jakymiw, A.; Fujita, D. J., Selected glimpses into the activation and function of Src kinase. *Oncogene* 2000, 19, (49), 5620-35.
31. Garaud, M.; Pei, D., Substrate profiling of protein tyrosine phosphatase PTP1B by screening a combinatorial peptide library. *J Am Chem Soc* 2007, 129, (17), 5366-7.

32. Qin, Zhaohong; Pandey, Nihar R.; Zhou, Xun; Stewart, Chloe; Hari, Aswin; Huang, Hua; Stewart, Alexandre; Brunel, Jean; Chen, Hsiao-Huei. Functional properties of Claramine: A novel PTP1B inhibitor and insulin-mimetic compound. *Biochemical and Biophysical Research Communications* 2015, 458, 21-27.
33. Lantz, Kristen A; Emeigh Hart, Susan G; Planey, Sonia L; Roitman, Mitchell F; Ruiz-White, Inez A; Wolfe, Henry R; McLane, Michael P. Inhibition of PTP1B by trodusquemine (MSI-1436) causes fat-specific weight loss in diet-induced obese mice. *Obesity* 2010 18, 1516-1523.
34. Balyasnikova, I. V.; Wainwright, D. A., et al., Characterization and immunotherapeutic implications for a novel antibody targeting interleukin (IL)-13 receptor alpha2. *J Biol Chem* 2012, 287, (36), 30215-27.
35. Newman, J. P.; Wang, G. Y., et al., Interleukin-13 receptor alpha 2 cooperates with EGFRvIII signaling to promote glioblastoma multiforme. *Nat Commun* 2017, 8, (1), 1913.
36. Yamada, M.; Chiba, T., et al., Implanted cannula-mediated repetitive administration of Abeta25-35 into the mouse cerebral ventricle effectively impairs spatial working memory. *Behav Brain Res* 2005, 164, (2), 139-46.

The invention claimed is:

1. A method of treatment of IL13Rα2-overexpressing cancer in a subject, wherein the treatment comprises administering to said subject an effective amount of a protein tyrosine phosphatase-1B (PTP1B) inhibitor, wherein the PTP1B inhibitor is Claramine, and wherein the cancer is glioblastoma (GBM), metastatic colorectal cancer (CRC), or ovarian cancer (OC).

2. The method according to claim 1, wherein the cancer is concomitant with invasion and metastasis formation.

* * * * *